United States Patent
Baek et al.

(10) Patent No.: US 10,525,017 B2
(45) Date of Patent: Jan. 7, 2020

(54) COMPOSITION CONTAINING MESO-2,3-BUTANEDIOL

(71) Applicant: Amorepacific Corporation, Seoul (KR)

(72) Inventors: Heung Soo Baek, Yongin-si (KR); Byeong Yung Woo, Yongin-si (KR); Se Jin Yoo, Yongin-si (KR); Yung Hyup Joo, Yongin-si (KR); Song Seok Shin, Yongin-si (KR); Mi Hyun Oh, Yongin-si (KR); John Hwan Lee, Yongin-si (KR); Seo Young Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 12 days.

(21) Appl. No.: 15/518,428

(22) PCT Filed: Oct. 21, 2015

(86) PCT No.: PCT/KR2015/011120
§ 371 (c)(1),
(2) Date: Apr. 11, 2017

(87) PCT Pub. No.: WO2016/064180
PCT Pub. Date: Apr. 28, 2016

(65) Prior Publication Data
US 2017/0312230 A1    Nov. 2, 2017

(30) Foreign Application Priority Data

Oct. 21, 2014    (KR) .......................... 10-2014-0142817
Oct. 21, 2014    (KR) .......................... 10-2014-0142818

(51) Int. Cl.
*A61K 31/047*    (2006.01)
*A61K 8/34*       (2006.01)
*A61Q 19/10*     (2006.01)
*A61K 8/30*       (2006.01)

(52) U.S. Cl.
CPC ............. *A61K 31/047* (2013.01); *A61K 8/30* (2013.01); *A61K 8/34* (2013.01); *A61Q 19/10* (2013.01)

(58) Field of Classification Search
None
See application file for complete search history.

(56) References Cited

U.S. PATENT DOCUMENTS 6,623,724 B2    9/2003    Brown et al.
2011/0177579 A1    7/2011    Ma et al.

FOREIGN PATENT DOCUMENTS

JP         2002-212021 A     7/2002
KR    10-2012-0007339 A     1/2012
WO         2012/124890 A2    9/2012

OTHER PUBLICATIONS

Wikipedia, "2,3-Butanediol", downloaded on Oct. 2, 2017 from "en.wikipedia.org/wiki/2,3-butanediol", 4 pages.*
Machine translation of the Description section of the JP 2002-212021 patent document previously cited, 11 pages; machine translation created Oct. 2, 2017.*
Herold et al., "Determination of the Three Isomers of 2,3-Butanediol Formed by Yeasts or Lactic Acid Bacteria During Fermentation", American Journal of Enology and Viticulture, 1995, vol. 46(1), pp. 134-137.*
"GS Caltex", Value No. 1 Energy & Chemical Partner, GS Caltex, Sustainability Report, 2013, pp. 1-51.
International Search Report for PCT/KR2015/011120 dated Feb. 3, 2016 [PCT/ISA/210].
Written Opinion for PCT/KR2015/011120 dated Feb. 3, 2016 [PCT/ISA/237].

* cited by examiner

*Primary Examiner* — Savitha M Rao
*Assistant Examiner* — Gregg Polansky
(74) *Attorney, Agent, or Firm* — Sughrue Mion, PLLC

(57) ABSTRACT

The present invention relates to a composition which can effectively control bacteria by containing meso-2,3-butanediol, which is an isomer of 2,3-butane diol, and has excellent antiseptic power even without containing a chemical antiseptic agent.

8 Claims, No Drawings

COMPOSITION CONTAINING MESO-2,3-BUTANEDIOL

CROSS REFERENCE TO RELATED APPLICATIONS

This application is a National Stage of International Application No. PCT/KR2015/011120 filed Oct. 21, 2015, claiming priority based on Korean Patent Application No. 10-2014-0142818 filed Oct. 21, 2014 and Korean Patent Application No. 10-2014-0142817 filed Oct. 21, 2014, the contents of all of which are incorporated herein by reference in their entirety.

TECHNICAL FIELD

The present invention relates to a composition which can effectively control bacteria by containing meso-2,3-butanediol that is an isomer of 2,3-butane diol, and has excellent antiseptic power even without containing a chemical antiseptic agent.

BACKGROUND OF ART

Microorganisms are living organisms that always exist around us, and there are beneficial microorganisms that help human beings, whereas there are harmful microorganisms that cause problems such as giving rise to disease, creating a bad smell and giving an aesthetic feeling of dislike. In particular, microorganisms may exist in the body such as hair, body, hand, foot and the like due to the external environment, and a large amount of microorganisms may exist even in pet hair and the like. In addition, microorganisms may exist in foods such as vegetables, fruits, fishes, cooking utensils, dishes, or cooking places, and further microorganisms may exist even in toilets. Like this, microorganisms always exist in many places around us.

Therefore, there is a need for an antibacterial agent for sterilizing and cleaning microorganisms for a safe and hygienic life, and various antibacterial agents have been developed accordingly.

On the other hand, an external composition for skin may be contaminated with microorganisms through various routes such as contamination by microorganisms that may occur during the manufacturing process, contamination of bacteria by skin contact of fingers during use, or contamination by water during use.

Therefore, it is required to formulate an antiseptic agent or the like in order to inhibit the growth of microorganisms in the composition or kill the microorganisms and to improve the preservability of the product.

Commonly used antiseptic agents include, for example, paraoxybenzoic acid esters (collectively referred to as "parabens"), imidazolidinyl urea, phenoxyethanol, chlorophenacin or the like. These chemical antiseptic agents may exhibit the effectiveness as antiseptic means for use in the external composition for skin. However, these chemical preservatives formulated in the composition may exhibit skin irritation, allergies, etc., and in severe cases it may exhibit skin toxicity.

It is also possible to prepare an external composition for skin which does not contain an antiseptic agent such as parabens or phenoxyethanol. In such a case, however, a separate measure or device is required for ensuring antiseptic power. For example, it can be aseptically manufactured, or the dosage or the period of use can be restricted. In some cases, it requires complicated means such as the use of a container placed little by little or a container not refilled (for example, a backless tube or a container with a dispenser) is required and thereby there is a problem that it is not economical.

On the other hand, it is known that some diols have an antiseptic power. For example, in the case of 1,2-butanediol and 1,2-hexanediol, the antiseptic power is excellent and thus they are partially used. However, 1,2-butanediol and 1,2-hexanediol have been restricted in their use for preservation of external preparations such as cosmetics due to safety problems such as skin irritation and irritation feeling.

PRIOR ART DOCUMENT

Patent Document 1. Korean Patent Laid-open Publication No. 10-2011-0058237 (published on Jun. 1, 2011)
Patent Document 2. Korean Patent Laid-open Publication No. 10-2003-0026065 (Published on Mar. 31, 2003)

DETAILED DESCRIPTION OF THE INVENTION

Technical Problem

Therefore, the present inventors have conducted intensive studies to find out an antiseptic substance which is highly safe to the skin while effectively controlling the bacteria present in the skin and the peripheral environment. As a result, the present inventors have found that meso-2,3-butanediol exhibits low irritation to skin while having excellent antibacterial and antiseptic activities, thereby completing the present invention.

Therefore, it is an object of the present invention to provide an antibacterial composition that can have high antibacterial activity and thus effectively control bacteria even when used in a small amount.

It is another object of the present invention to provide an external composition for skin containing an antiseptic component which has high safety for skin and feeling of use while having high antiseptic powder and thereby replacing an existing chemical antiseptic agent.

Technical Solution

In order to achieve these objects, the present invention provides a composition containing meso-2,3-butanediol represented by the chemical formula 1 below.

[Chemical Formula 1]

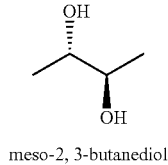

meso-2, 3-butanediol

The present invention also provides use of meso-2,3-butanediol as an antibacterial agent in an antibacterial composition.

In addition, the present invention provides use of meso-2,3-butanediol as an antiseptic agent in an external preparation composition for skin.

Advantageous Effects

The composition containing meso-2,3-butanediol according to the present invention exhibits excellent antibacterial effects even when used in a small amount, and thereby can alleviate and improve skin diseases such as various eczema infected by bacteria and mold. Further, the composition containing meso-2,3-butanediol according to the present invention exhibits sufficient antiseptic power without using a conventional chemical antiseptic agent that reduces a safety for skin due to a high irritation, and at the same time it has an advantage that the stability for skin and the feeling of use are superior, and therefore it can be widely utilized in the field of cosmetics and the like.

DETAILED DESCRIPTION OF THE EMBODIMENTS

The present invention provides a composition containing meso-2,3-butanediol.

Particularly, the present invention provides an antibacterial composition, more particularly, an antibacterial detergent composition, containing meso-2,3-butanediol.

Further, the present invention provides an external preparation composition for skin containing meso-2,3-butanediol as an antiseptic agent.

2,3-Butanediol is generally produced by fermentation, and for example, is produced by bacteria such as *Klebsiella pneumoniae, Bacillus polymyxa, Enterobacter aerogenes*, etc., and is chemically synthesized by using pentose, xylose and arabinose or the like as a raw material.

In particular, in the external preparation for skin such as cosmetics, 2,3-butanediol is typically included in the composition as components such as emollients, humectants or wetting agents.

2,3-Butanediol can be classified into three isomers from the viewpoint of stereochemistry. That is, it can be classified into meso-2,3-butanediol, S,S-2,3-butanediol, and R,R-2,3-butanediol, and the respective structures thereof are represented by the chemical formulas 1 to 3 below.

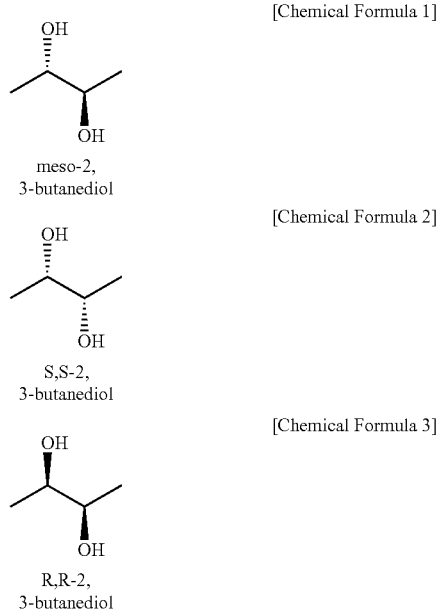

[Chemical Formula 1]
meso-2,3-butanediol

[Chemical Formula 2]
S,S-2,3-butanediol

[Chemical Formula 3]
R,R-2,3-butanediol

The present inventors have found that, among the three stereoisomers of 2,3-butanediol, especially meso-2,3-butanediol has less irritation to skin while having higher antibacterial activity and superior antiseptic power, as compared with other stereoisomers.

Therefore, one embodiment of the present invention can provide a composition containing meso-2,3-butanediol having an antibacterial activity and thereby exhibiting excellent antibacterial activity even when used in a small amount.

In addition, according to the present invention, as an alternative to a chemical antiseptic agent, there may be provided a composition using meso-2,3-butanediol having antibacterial activity as an antiseptic agent, thereby having less irritation feeling as compared with a conventional composition using a chemical antiseptic agent such as parabens, imidazolidinyl urea or phenoxyethanol, and diols such as 2-butanediol or 1,2-hexanediol.

In addition, by controlling the compounding amount of meso-2,3-butanediol according to a desired use purpose, sufficient antiseptic property and preservation power can be ensured without mixing a chemical antiseptic agent at all, and in particular, when used in cosmetics, it is excellent in safety for skin and usability, and further has an excellent affinity with other components of the cosmetics.

In the present invention, "antibacterial" means resistance to all contaminant microorganisms such as bacteria, molds, and yeasts, including the meaning of both antimicrobial and antifungal. The "antibacterial activity" means a defense capacity against these contaminant microorganisms.

In the present invention, the term "external preparation composition for skin" refers to including overall compositions commonly used for skin external application. For example, it refers to various cosmetics such as basic cosmetics, makeup cosmetics, and hair cosmetics (including body products); or a composition widely applicable to various pharmaceuticals or quasi-drugs such as ointment preparations. The present invention provides an external composition of these forms individually.

In the present invention, the "antiseptic" refers to preventing a phenomenon where a product is contaminated and thus a substance is deteriorated due to proliferation of contaminant microorganisms such as bacteria, molds or yeasts in the product, and stably storing a composition for a long period of time. The "antiseptic power" means an ability to prevent the products from being contaminated due to peripheral contamination sources such as these contaminant microorganisms and thereby the substances from being deteriorated.

In the present invention, in order to effectively exhibit a desired effect, meso-2,3-butanediol is used in an amount of 0.001% by weight or more, preferably 0.5% by weight or more, particularly 1.0% by weight or more, more preferably 1.5% by weight or more, based the total weight of the composition. Further, taking into account the efficiency due to the mixing of the other components in the composition in an effective amount and the mixing of meso-2,3-butanediol, the content of meso-2,3-butanediol is limited to 20% by weight or less, or 10% by weight or less.

Further, more preferably, in the antibacterial composition containing meso-2,3-butanediol, the meso-2,3-butanediol can be contained in an amount of 2.0 to 10% by weight based on the total weight of the composition.

Further, still more preferably, in the external preparation composition for skin containing meso-2,3-butanediol as an antiseptic agent, the meso-2,3-butanediol can be contained in an amount of 1.5 to 4% by weight based on the total weight of the composition.

The meso-2,3-butanediol used in the composition of the present invention can be commonly produced using conventional methods and incorporated in the composition, or a commercially available product may be incorporated in the composition.

When considering only the desired effects of the present invention as described above, it is not necessary to add and incorporate other antibacterial agents or antiseptic agents in the external preparation composition of the present invention, but other antibacterial agents commonly used in the external preparation composition may be further added to the external composition of the present invention within the range of not impairing the above effect. In addition, in the composition of the present invention, insofar as a desired effect is not inhibited, it is possible to add components commonly incorporated in external preparations, for example, humectants, ultraviolet absorbers, vitamins, animal and plant extract components, digestive agents, whitening agents, vasodilators, astringents, refreshing agents, hormonal agents, and the like, depending on the properties of the external composition.

The composition of the present invention may be an external preparation composition for skin, specifically, a cosmetic composition, a pharmaceutical composition and the like. In addition, the above-mentioned composition may be formulated in the form of, for example, a makeup cosmetic, a skin lotion, a cream, a lotion, an essence or a pack, more particularly, it may be formulated in the form of a softening skin lotion, an astringent skin tonic, a skin nutrition lotion, a lotion, an eye cream, a nutrition cream, a massage cream, a cleansing cream, a cleansing foam, a cleansing water, a powder, a foundation, a makeup base, an essence or a pack, and their preparation is not particularly limited. Further, in each preparation, other components can be appropriately selected and incorporated by those skilled in the art without difficulty, in accordance with the type of other compositions or the purpose of use.

When the composition of the present invention is an antibacterial composition, it may be preferably formulated into a detergent composition, and its preparation is not particularly limited, but specifically it may be formulated into a hand sanitizer, a hand wash, a body wash, a cleansing cream, a cleansing gel, a cleansing foam, a cleansing water, a soap, a wet tissue, and the like.

In addition, the composition of the present invention can be formulated in a form that can be easily applied to the peripheral environment, for example, in the form of a spray, a wet tissue and the like.

Hereinafter, the present invention will be described in more detail with reference to preferred test examples. However, the following test examples are for confirming the effect of the present invention by way of example, and the scope of the present invention is not limited thereto.

[Test Example 1] Antibacterial Activity Test

In order to compare the antibacterial activities by the position and stereoscopic orientation of the hydroxyl group of the diol, the antibacterial activities (minimum inhibitory concentration, MIC) against the samples described in Table 1 below, that is, six kinds of diols such as 1,3-butanediol, were measured.

The antibacterial activity measurement tests were performed using bacteria, yeasts and molds, such as *Escherichia coli* (ATCC 8739), *Pseudomonas aeruginosa* (ATCC 9027), *Staphylococcus aureus* (ATCC 6538), *Candida albicans* (ATCC 10231), and *Aspergillus niger* (ATCC 16404). Respective substances or the like were added to Tryptic Soy broth and Sabouraud Dextrose (SD) broth at a concentration of 0.01 to 10% (v/v), the culture solution was prepared in a liquid phase, and the bacteria, yeasts, and molds were inoculated, and then cultured at 25 to 32° C. for 24 to 72 hours to observe the state of the bacteria. Thus determined MICs of the six tested materials are shown in Table 1.

TABLE 1

| Test Material | E. coli | P. aeruginosa | S. aureus | C. albicans | A. niger |
|---|---|---|---|---|---|
| 1,3-butanediol | >10 | >10 | >10 | >10 | >10 |
| 1,2-butanediol | 5 | 2.5 | 1.25 | 5 | 2.5 |
| S,S-2,3-butanediol | 5 | 5 | 2.5 | 5 | 1.25 |
| R,R-2,3-butanediol | 2.5 | 5 | 10 | 5 | 5 |
| Meso-2,3-butanediol | 1.25 | 2.5 | 5 | 2.5 | 1.25 |
| 1,2-hexanediol | 1.25 | 1.25 | 2.5 | 1.25 | 0.625 |

Looking at the results of Table 1, the antibacterial activity of the diols appeared to differ depending on the position of a hydroxy group, and it was confirmed that the mezo-2,3-butanediol used in the present invention had excellent antibacterial activity.

[Formulation Examples 1 to 9 and Comparative Formulation Examples 1 to 4] Skin Nutrition Lotion (Lotions)

Samples of Formulation Examples 1 to 9 containing meso-2,3-butanediol, and samples of Comparative Formulation Examples 1 to 4, not containing meso-2,3-butanediol (Comparative Formulation Example 1), or alternatively containing existing 1,2-hexanediol (Comparative Formulation Examples 2 and 3) or methylparaben as a conventional antiseptic agent (Comparative Formulation Example 4) were prepared by a conventional method, using the composition of Table 2 below.

TABLE 2

| Material name | Formulation Example | | | | | | | | | Comparative Formulation Example | | | |
|---|---|---|---|---|---|---|---|---|---|---|---|---|---|
| | 1 | 2 | 3 | 4 | 5 | 6 | 7 | 8 | 9 | 1 | 2 | 3 | 4 |
| Purified water | Balance | Balance | Balance | Balance | Balance | Balance | Balance | Balance | Balance | Balance | Balance | Balance | Balance |
| Liquid paraffin | 5.0 | 5.0 | 5.0 | 5.0 | 5.0 | 5.0 | 5.0 | 5.0 | 5.0 | 5.0 | 5.0 | 5.0 | 5.0 |
| Glycerin | 5.0 | 5.0 | 5.0 | 5.0 | 5.0 | 5.0 | 5.0 | 5.0 | 5.0 | 5.0 | 5.0 | 5.0 | 5.0 |
| Cetyl octanoate | 5.0 | 5.0 | 5.0 | 5.0 | 5.0 | 5.0 | 5.0 | 5.0 | 5.0 | 5.0 | 5.0 | 5.0 | 5.0 |
| Concentrated glycerin | 3.0 | 3.0 | 3.0 | 3.0 | 3.0 | 3.0 | 3.0 | 3.0 | 3.0 | 3.0 | 3.0 | 3.0 | 3.0 |

TABLE 2-continued

| Material name | Formulation Example | | | | | | | | | Comparative Formulation Example | | | |
|---|---|---|---|---|---|---|---|---|---|---|---|---|---|
| | 1 | 2 | 3 | 4 | 5 | 6 | 7 | 8 | 9 | 1 | 2 | 3 | 4 |
| Cyclomethicone | 2.0 | 2.0 | 2.0 | 2.0 | 2.0 | 2.0 | 2.0 | 2.0 | 2.0 | 2.0 | 2.0 | 2.0 | 2.0 |
| Dimethicone | 1.0 | 1.0 | 1.0 | 1.0 | 1.0 | 1.0 | 1.0 | 1.0 | 1.0 | 1.0 | 1.0 | 1.0 | 1.0 |
| Stearic acid | 0.8 | 0.8 | 0.8 | 0.8 | 0.8 | 0.8 | 0.8 | 0.8 | 0.8 | 0.8 | 0.8 | 0.8 | 0.8 |
| Cetostearyl alcohol | 0.7 | 0.7 | 0.7 | 0.7 | 0.7 | 0.7 | 0.7 | 0.7 | 0.7 | 0.7 | 0.7 | 0.7 | 0.7 |
| Glycerin stearate | 0.6 | 0.6 | 0.6 | 0.6 | 0.6 | 0.6 | 0.6 | 0.6 | 0.6 | 0.6 | 0.6 | 0.6 | 0.6 |
| Triethanol amine | 0.2 | 0.2 | 0.2 | 0.2 | 0.2 | 0.2 | 0.2 | 0.2 | 0.2 | 0.2 | 0.2 | 0.2 | 0.2 |
| Carboxy vinyl polymer | 0.15 | 0.15 | 0.15 | 0.15 | 0.15 | 0.15 | 0.15 | 0.15 | 0.15 | 0.15 | 0.15 | 0.15 | 0.15 |
| Sodium ethylene diamine acetate | 0.02 | 0.02 | 0.02 | 0.02 | 0.02 | 0.02 | 0.02 | 0.02 | 0.02 | 0.02 | 0.02 | 0.02 | 0.02 |
| Perfume | Proper amount | Proper amount | Proper amount | Proper amount | Proper amount | Proper amount | Proper amount | Proper amount | Proper amount | Proper amount | Proper amount | Proper amount | Proper amount |
| Meso-2,3-butanediol | 0.5 | 1 | 1.5 | 2 | 3 | 4 | 5 | 10 | 12 | — | — | — | — |
| 1,2-hexanediol | — | — | — | — | — | — | — | — | — | — | 0.5 | 1 | — |
| Methylparaben | — | — | — | — | — | — | — | — | — | — | — | — | 0.5 |

[Test Example 2] Antiseptic Power Test

In order to evaluate the antiseptic power, 20 g of the cosmetics of Formulation Examples 1 to 9 and Comparative Formulation Examples 1 to 4 were added to the mixed bacteria solution of *Escherichia coli* (ATCC 8739), *Staphylococcus aureus* (ATCC 6538), *Pseudomonas aeruginosa* (ATCC 99027) and the like so that the initial concentration was $10^6$ cfu (colony forming unit)/g per sample. While culturing the mixture in a thermostatic chamber at 22.5° C. for 4 weeks, 1 g of each cosmetic was taken at intervals of 1, 7, 14, 21 and 28 days, and the viable cell count was measured. The results are shown in Table 3 below.

In the case of molds, a mixed bacteria solution of *Penicillium citrinum* (ATCC 9849) and *Aspergillus niger* (ATCC 16404) was added so as to have an initial concentration of $10^6$ cfu/g per sample. Subsequently, while culturing the mixture in a thermostatic chamber at 25° C., the presence or absence of unpleasant odor and the presence or absence of hyphae and spores on the surface of the sample were observed at intervals of 7 days. The results are shown in Table 3 below.

TABLE 3

| Cosmetics | Bacteria (cfu/g) | | | | | | |
|---|---|---|---|---|---|---|---|
| Initial number of bacteria | Initial number of bacteria | 1 days | 7 days | 14 days | 21 days | 28 days | Molds* |
| Preparation Example 1 | 1 × 10⁶ | 1425 | <1000 | <1000 | <1000 | <1000 | + |
| Preparation Example 2 | 1 × 10⁶ | 1324 | <1000 | <100 | <100 | <10 | − |
| Preparation Example 3 | 1 × 10⁶ | <1000 | <100 | <10 | <10 | <10 | − |
| Preparation Example 4 | 1 × 10⁶ | <1000 | <100 | <10 | <10 | <10 | − |
| Preparation Example 5 | 1 × 10⁶ | <100 | <10 | <10 | <10 | <10 | − |
| Preparation Example 6 | 1 × 10⁶ | <10 | <10 | <10 | <10 | <10 | − |
| Preparation Example 7 | 1 × 10⁶ | <10 | <10 | <10 | <10 | <10 | − |
| Preparation Example 8 | 1 × 10⁶ | <10 | <10 | <10 | <10 | <10 | − |
| Preparation Example 9 | 1 × 10⁶ | <10 | <10 | <10 | <10 | <10 | − |
| Comparative Preparation Example 1 | 1 × 10⁶ | 2200 | 10000 | 4000 | 3500 | <1000 | ++ |
| Comparative Preparation Example 2 | 1 × 10⁶ | 1250 | <1000 | <10 | <10 | <10 | − |

TABLE 3-continued

| Cosmetics | Bacteria (cfu/g) | | | | | | |
|---|---|---|---|---|---|---|---|
| Initial number of bacteria | Initial number of bacteria | 1 days | 7 days | 14 days | 21 days | 28 days | Molds* |
| Comparative Preparation Example 3 | $1 \times 10^6$ | 1000 | 100 | <10 | <10 | <10 | – |
| Comparative Preparation Example 4 | $1 \times 10^6$ | <10 | <10 | <10 | <10 | <10 | – |

−: No occurrence of unpleasant odor, hyphae and spores for 8 weeks, and excellent
+: Occurrence of molds on a vessel wall and lid within 4 weeks
++: Occurrence of unpleasant odor and molds on the partial surface within 4 weeks
+++: Occurrence of unpleasant odor and molds on the whole surface within 4 weeks From the results of Table 3 above, it was confirmed that the preparation examples using meso-2,3-butanediol could represent the antiseptic effect, particularly, when meso-2,3-butanediol was contained in an amount of 1.5% by weight or more (Formulation Examples 3 and 4), it exhibited an antiseptic power similar to or superior to Comparative Formulation Examples 2 and 3 using conventional 1,2-hexanediol as an antiseptic agent, and when meso-2,3-butanediol was contained in an amount of 4% by weight or more (Formulation Examples 6 to 9), it exhibited very excellent antiseptic power which was comparable to as that of Comparative Formulation Example 4 using an existing methylparaben as an antiseptic agent.

[Test Example 3] Usability (Feeling of Irritation) Test

Experiments were conducted to evaluate the feeling of irritation on the samples of Formulation Example 6 and Comparative Formulation Examples 1 to 4 and the like. Specifically, 0.5 ml of samples of Preparation Example 6 and Comparative Formulation Examples 1 to 4 were applied to 15 panelists, respectively, while randomly changing left and right. After rubbing the samples and the like on the skin, a feeling of irritation such as "stinging" and "burning" were evaluated, and the results are shown in Table 4 below <Evaluation Criteria>
0 to 0.4: None
0.4 to 1.0: Slight
1.1 to 2.0: Moderate
2.1 to 3.0: Severe

TABLE 4

| | Test material | | | | |
|---|---|---|---|---|---|
| | Preparation Example 6 | Comparative Preparation Example 1 | Comparative Preparation Example 2 | Comparative Preparation Example 3 | Comparative Preparation Example 4 |
| Stinging | 0.19 | 0.20 | 0.32 | 0.38 | 0.92 |
| Burning | 0.62 | 0.54 | 0.79 | 0.94 | 0.85 |
| Average | 0.41 | 0.37 | 0.56 | 0.66 | 0.89 |

As can be seen from Table 4, it was confirmed that, although Preparation Example 6 used a larger amount of meso-2,3-butanediol as an antiseptic agent, the degree of irritation was much lower as compared with Comparative Formulation Examples 2 and 3 using existing 1,2-hexanediol and Comparative Formulation Example 4 using existing methylparaben antiseptic agent.

[Test Example 4] Skin Irritation Test

In order to evaluate the skin safety of a human body on 1,3-butanediol, 1,2-butanediol and 1,2-hexanediol (conventionally used diol), which are similar to meso-2,3-butanediol, S,S-2,3-butanediol and R,R-2,3-butanediol that are stereoisomers of 2,3-butanediol except that the position of a hydroxy group is different, the patch test was carried out for 24 hours. The patch was attached to the upper part of the subject's back, and 20 μl of the prepared test substance was applied to the patch using an IQ chamber (chemotechique, Sweeden). The patch was attached and after the lapse of 24 hours, the patch was removed. After removal of the patch, the first reading was performed after 30 minutes, and the second reading was performed after 24 hours.

In order to investigate the intensity of the skin irritation of the samples, weighting values were given according to the degree of positive reaction of the skin, skin average reactivity was determined, and the skin irritation of the sample was judged. The skin average reactivity was calculated using the mathematical formula 1 below, and the determination criteria are as shown in Table 5 below. The experimental results are shown in Table 6 below.

$$\text{Score} = \frac{\Sigma \text{Grade} \times \text{No. of responses} \times 100}{4(\text{Maximum grade}) \times n(\text{No. of total subjects}) \times 2(\text{No. of visual scoring})} \quad \text{[Methematical Formula 1]}$$

TABLE 5

| Score | Skin irritation intensity |
|---|---|
| Less than 1 (Grade I) | No irritation |
| More than 1 and less than 3 (Grade II) | Mild irritation |
| More than 3 and less than 5 (Grade III) | Moderate irritation |
| More than 5 (Grade IV) | Moderate irritation |

TABLE 6

| Test material | Content (%) | Score |
|---|---|---|
| Purified water | 100 | 0.32 |
| 1,3-butanediol | 30 | 0.52 |
| 1,2-butanediol | 30 | 2.48 |
| S,S-2,3-butanediol | 30 | 2.12 |
| R,R-2,3-butanediol | 30 | 1.45 |
| Meso-2,3-butanediol | 30 | 0.41 |
| 1,2-hexanediol | 20 | 2.54 |

From the results in Table 6, it was confirmed that meso-2,3-butanediol was lower in numerical value of skin irritation even when used in a larger amount than 1,2-hexanediol, and that the numerical value of skin irritation was lower even compared with S,S-2,3-butanediol and R,R-2,3-butanediol that are the other stereoisomers.

Through the above Test Examples and the like, the external preparation composition for skin according to the present invention uses meso-2,3-butanediol that is a stereochemical isomer, and thereby has excellent antiseptic power even without using a conventional chemical antiseptic agent or 1,2-hexanediol, and at the same time the level of skin irritation or the feeling of irritation is much lower than conventional chemical antiseptic agent or 1,2-hexanediol and thereby, the feeling of use is improved, the antibacterial activity is excellent and bacteria is effectively controlled even when used in a small amount.

The invention claimed is:

1. A cleansing composition containing a 2,3-butanediol in an amount of 1.5% to 4% by weight based on the total weight of the cleansing composition,
    wherein the 2,3-butanediol consists of meso-2,3-butanediol of the chemical formula 1 below:

Chemical Formula 1

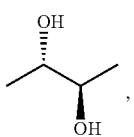

and
    wherein the cleansing composition is in a form of a cosmetic pack, a hand sanitizer, a hand wash, a body wash, a cleansing cream, a cleansing gel, a cleansing foam, a cleansing water, a soap, or a wet tissue,
    provided that the cleansing composition does not contain 2S,3S-butanediol and 2R,3R-butanediol isomeric forms.

2. The cleansing composition according to claim 1, wherein the composition is an antibacterial composition.

3. The cleansing composition according to claim 1, wherein the cleansing composition is in a formulation selected from the group consisting of a hand sanitizer, a hand wash, a body wash, a soap, and a wet tissue.

4. A dermatological antiseptic composition comprising a 2,3-butanediol as an antiseptic agent in an amount of 1.5% to 4% by weight based on the total weight of the dermatological antiseptic composition,
    wherein the 2,3-butanediol consists of meso 2,3-butanediol of the following chemical formula 1 below:

[Chemical Formula 1]

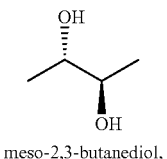

meso-2,3-butanediol, provided that the dermatological composition does not contain 2S,3S-butanediol and 2R,3R-butanediol isomeric forms.

5. The dermatological antiseptic composition according to claim 4, wherein the dermatological antiseptic composition is in a cosmetic formulation in a form selected from the group consisting of a cream, a lotion, a powder, an essence, and a face pack.

6. The cleansing composition according to claim 1, wherein the cleansing composition is an external composition which is applied to skin and is a cosmetic composition.

7. A method for cleaning skin of human, comprising applying the cleansing composition of claim 1 to the skin.

8. A method for cleaning skin of human, comprising applying the dermatological antiseptic composition of claim 4 to the skin.

* * * * *